(12) United States Patent
Faldt et al.

(10) Patent No.: US 10,946,183 B2
(45) Date of Patent: Mar. 16, 2021

(54) ASEPTIC CONNECTOR

(71) Applicant: Cytiva Sweden AB, Uppsala (SE)

(72) Inventors: Eric Faldt, Uppsala (SE); Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 0 days.

(21) Appl. No.: 15/625,401

(22) Filed: Jun. 16, 2017

(65) Prior Publication Data
US 2017/0281921 A1 Oct. 5, 2017

Related U.S. Application Data

(62) Division of application No. 14/385,307, filed as application No. PCT/SE2013/050328 on Mar. 25, 2013, now abandoned.

(30) Foreign Application Priority Data

Mar. 27, 2012 (SE) ...................................... 1250301

(51) Int. Cl.
*A61M 39/10* (2006.01)
*A61M 39/16* (2006.01)
(Continued)

(52) U.S. Cl.
CPC .......... *A61M 39/105* (2013.01); *A61M 39/16* (2013.01); *A61M 39/18* (2013.01); *F16L 39/00* (2013.01); *F16L 2201/44* (2013.01)

(58) Field of Classification Search
CPC combination set(s) only.
See application file for complete search history.

(56) References Cited

U.S. PATENT DOCUMENTS 3,865,411 A   2/1975  Rowe et al.
3,909,910 A   10/1975 Rowe et al.
(Continued)

FOREIGN PATENT DOCUMENTS

EP   2148121       1/2010
WO   2009081196    7/2009
(Continued)

*Primary Examiner* — Brian E Glessner
*Assistant Examiner* — Daniel J Kenny
(74) *Attorney, Agent, or Firm* — Eversheds Sutherland (US) LLP

(57) ABSTRACT

The invention relates to a An aseptic connector comprising a first connection unit (102; 202; 302; 402; 502) provided with a first terminal end surface (104; 204; 304; 404; 504) and a second connection unit (106; 206; 306; 406; 506) provided with a second terminal end surface (108; 208; 308; 408; 508); said first and second terminal end surfaces are each provided with at least one first and second opening (110, 112; 210, 212; 310, 312; 410, 412; 510, 512), which openings are orientated to substantially coincide when said first and second connection units are connected to each other; said first and second openings are sealed by at least one film (114; 214; 314; 414; 514) arranged on said first and second connection units, so that the contact between the film and each connection unit is aseptic; said at least one film is adapted to be mated with a corresponding film on the other connection unit when said first and second connection units are connected to each other; and said mated films are adapted to be pulled out together two and two after mating such that corresponding first and second openings in said first and second terminal end surfaces are mated aseptically. At least two first ports (116; 216; 316; 416; 516) are arranged on the first connection unit, which first ports have fluid connection with the at least one first opening (110; 210; 310; 410; 510) in the first terminal end surface; and in that at least one second port (118; 218; 318; 418; 518) is arranged
(Continued)

on the second connection unit, which the at least one second port has a fluid connection with the at least one second opening (112; 212; 312; 412; 512) in the second terminal end surface.

18 Claims, 8 Drawing Sheets

(51) Int. Cl.
*F16L 39/00* (2006.01)
*A61M 39/18* (2006.01)

(56) References Cited

U.S. PATENT DOCUMENTS

| | | | | |
|---|---|---|---|---|
| 4,019,512 A * | 4/1977 | Tenczar | ................ | A61M 39/14 222/80 |
| 4,022,205 A * | 5/1977 | Tenczar | ................ | A61M 39/14 138/109 |
| 4,030,494 A | 6/1977 | Tenczar | | |
| 4,418,945 A | 12/1983 | Kellogg | | |
| 5,116,315 A * | 5/1992 | Capozzi | ........... | A61B 17/00491 222/137 |
| 6,679,529 B2 | 1/2004 | Johnson et al. | | |
| 6,701,774 B2 | 3/2004 | Srinivasan et al. | | |
| 7,678,096 B2 * | 3/2010 | Biddel | .................. | A61M 39/16 604/403 |
| 7,758,560 B2 * | 7/2010 | Connell | .................... | A61J 1/20 222/1 |
| 7,922,211 B2 * | 4/2011 | .ANG.rthun | .......... | A61M 39/18 285/67 |
| 8,163,237 B2 * | 4/2012 | Crawford | .......... | A61M 5/16836 116/206 |
| 8,587,410 B2 | 11/2013 | Potyrailo et al. | | |
| 9,027,968 B2 * | 5/2015 | Gerst | ...................... | F16L 37/30 251/149.1 |
| 9,242,846 B2 * | 1/2016 | Burns | ................. | B67D 3/0058 |
| 2013/0048111 A1 | 2/2013 | Gebauer | | |
| 2015/0061282 A1 | 3/2015 | Faldt | | |

FOREIGN PATENT DOCUMENTS

| | | |
|---|---|---|
| WO | 2010087764 A1 | 8/2010 |
| WO | 2011079226 | 6/2011 |
| WO | 2011084101 | 7/2011 |

* cited by examiner

ASEPTIC CONNECTOR

TECHNICAL FIELD

The present invention relates to an aseptic connector according to the preamble of claim 1 and a first connection unit for such an aseptic connector according to the preamble of claim 11.

Such an aseptic connector is arranged for creating aseptic and sterile connections in sterile and in non-sterile environments.

BACKGROUND ART

The biotechnology industry uses different manufacturing systems for creating aseptic and sterile connections between process containers and equipment, such as plastic bags and pumps. A known manufacturing system uses controlled environments such as clean rooms or cabinets to ensure aseptic connections during manufacture. When necessary connections are made in such a controlled environment that breaches sterile tubing and piping, the environment does not contaminate the fluid flow passage. However, maintaining a clean room is time consuming, difficult and costly to validate.

Another known manufacturing system uses disposable plastic bags connected to flexible thermoplastic tubes, which requires special connections to assure that the bags and tubes remain clean and sterile. A sterile tube welding machine can be used to weld the thermoplastic tubing in a sterile manner without the need for a clean room, a laminar flow cabinet or similar environmental control device. After the thermoplastic tubes cool, a sterile weld is formed. A tube welding machine is however also usually limited in applicability to specific tube size and materials, such as thermoplastic. Furthermore, tube welding machines are typically large, heavy, lack versatility, and expensive.

Known are also pre-sterile bags and tube sets which can be supplied with the appropriate disposable aseptic connection system fittings already in place. These, connections are simple, repeatable and validatable.

Single use systems, also called disposable systems are more and more used in the bioprocess industry. For example separation or reaction systems such as chromatography systems, filter systems or bioreactor systems have today at least partly been provided as disposable systems. This eliminates the need for cleaning and cleaning validation before processing, in between processes and cycles or after processing before re-use as required for conventional re-usable equipment. With disposable systems cross-contamination is avoided.

Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilisation processes (gamma irradiation). The demands of the level of bioburden control can differ for different applications. However, bioburden control to a certain degree of the equipment is not only required for some applications, but also considered as the preferable for most of the applications using disposable equipment. The production of this equipment in controlled environments is required to guarantee a low initial level of contaminants prior to the bioburden control procedure. Sterility and asepsis are terms used to define the state of a system, a piece of equipment or a fluid conduit as being in control of bioburden levels to different degrees.

Prior art describes varying apparatus for accomplishing sterile connections using a disposable aseptic connection system.

Document U.S. Pat. No. 6,679,529 discloses an apparatus for establishing an aseptic and sterile connection comprising a sterile barrier enclosing a terminal end of a conduit, a resilient, deformable support card fixed to the sterile barrier having an outer face disposed about the terminal end of the conduit having an adhesive perimeter covered by a release paper, and a rolling membrane comprising a continuous, removable, yieldable, flexible strip material, a portion of which is removably adhered to the support card and overlies the end of the conduit, the rolling membrane having a free end whereby a force applied to the free end thereof withdraws the entire rolling membrane to expose the end of the conduit whereby an aseptic/sterile connection is achieved by adhering opposing support cards together, removing the rolling membrane thereby creating a sterile corridor between a first sterile barrier and a second sterile barrier, and mating the terminal end of a first conduit and a second conduit together.

WO2011/084101 A1 discloses stackable separation elements with folded films for establishing sterile connection between the elements. These elements are however not suitable for connecting complex systems of apparatuses and tubing. They are further not suitable for establishing separate connections for a plurality of fluids.

Notwithstanding the existence of such prior art apparatus for establishing an aseptic and sterile connection, there is a need for an improved and more efficient apparatus that can be used as either a temporary or permanent connection.

When a large number of equipment is connected to a process container it requires a large number of such prior art apparatuses for establishing an aseptic and sterile connection for each tubing to be connected individually. The physical size increases and ease of use reduces. The number of apparatuses and tubing are often perceived as a hazzle which will be complicated to handle.

SUMMARY OF THE INVENTION

An objective problem to be solved by the present invention is to reduce the number of such prior art apparatuses when a large number of equipment has to be connected to a process container.

Another objective problem to be solved by the present invention is to provide a connection that is reliable and repeatable.

A further objective problem to be solved by the invention is to provide multiple aseptic connections for a plurality of different fluids in one connector.

A further objective problem to be solved by the invention is to provide an aseptically connectable manifold for distributing or collecting a fluid to/from a plurality of containers.

A further objective problem to be solved by the present invention is to provide an aseptic connector which is applicable to a wide array of tubing sizes.

A further objective problem to be solved by the present invention is to provide an aseptic connector that is inexpensive to assemble and maintain and requires no complicated equipment to assemble.

A further objective problem to be solved by the present invention is to provide an aseptic connector that is compatible with the standard sanitary fittings common to the biotechnology industry.

These objects above are achieved by an aseptic connector according to claim 1 and a first connection unit for such an aseptic connector according to claim 11.

Since at least two first ports are arranged on the first connection unit at least two equipments can be connected to for example a process container using only one aseptic connector.

When a large number of equipment is connected to a process container a reduced number of aseptic connectors for establishing the aseptic and sterile connection for each pipe or tube can be achieved. The physical size decreases and ease of use increases. The number of apparatuses and tubing will be less complicated to handle.

With this invention any desired number of containers, bags, pumps and other equipment can be connected to each other in a system in an aseptic way which reduces the number of aseptic connectors. Furthermore, these systems can be built in an environment that is not bioburden controlled and the system with all its connections will still be aseptic on process side.

Since at least one second port is arranged on the second connection unit an aseptic connector arranged as manifold may be achieved.

According to an aspect of the invention the number of openings in the terminal end surface corresponds to the number of ports arranged on the connection unit. This configuration facilitates the connection of containers, bags, pumps and other equipment that can be connected to each other and also reduces the number of aseptic connectors.

A further aspect of the invention is to provide a sterile circuit, comprising a first connection unit, fluidically connected with at least two lengths of tubing. This is achieved with a sterile cirquit according to the claims. An advantage of this is that the setup of complex sterile systems is facilitated. A further advantage is fluid supply and removal systems for e.g. screening systems with a plurality of bioreactors can be made compact and easily handled.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

Further aspects, advantages and features of the invention can be derived from the following detailed description of exemplary embodiments of the invention, with reference to the drawings.

DETAILED DESCRIPTION

Figure 1:
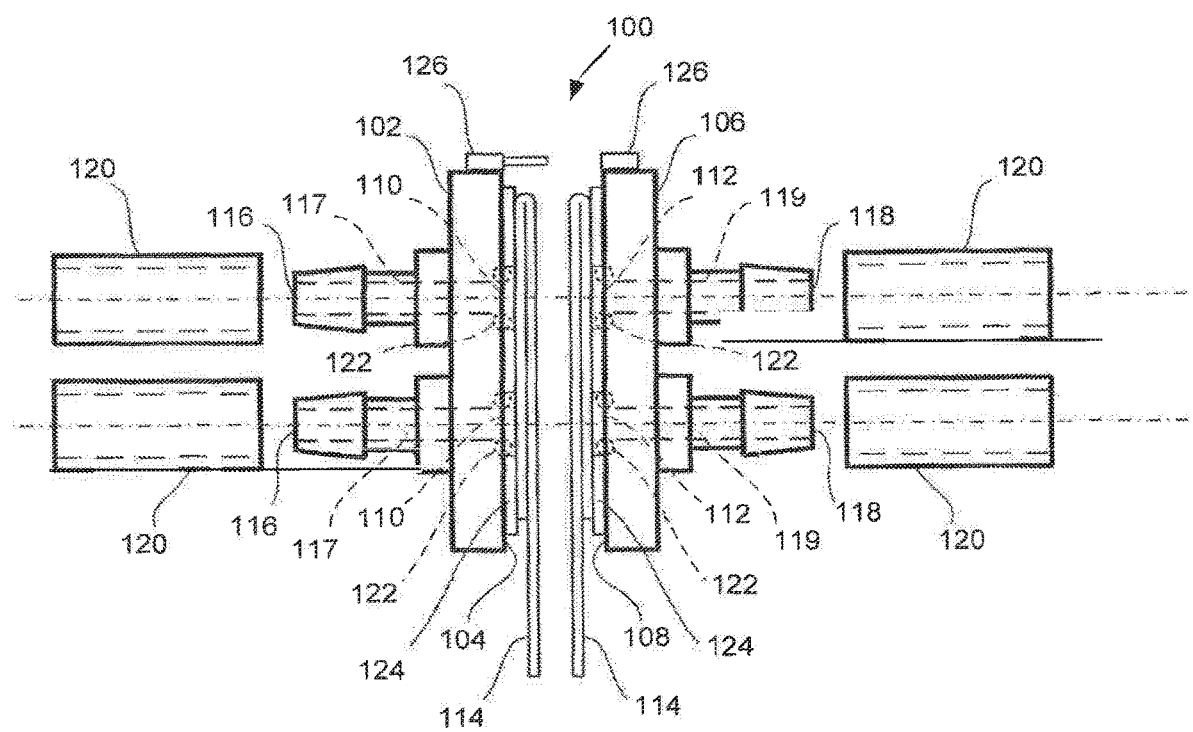
FIG. 1 shows a side view of a first embodiment of an aseptic connector according to the invention.

FIG. 1 shows a first embodiment of an aseptic connector 100 comprising a first connection unit 102 provided with a first terminal end surface 104 and a second connection unit 106 provided with a second terminal end surface 108. Said first and second terminal end surfaces 104, 108 are each provided with at least one first and second opening 110, 112. In the first embodiment two first openings 110 are arranged in the first terminal end surface 104 and two second openings 112 are arranged in the second terminal end surface 108.

The first and second openings 110, 112 are sealed by at least one film 114 arranged on said first and second connection units 102, 106. The contact surfaces between the film 114 and each connection unit 102, 104 are aseptic. The film 114 is adapted to be mated with a corresponding film 114 on the other connection unit when said first and second connection units 102, 104 are connected to each other. Thereafter, the mated films 114 are adapted to be pulled out together two and two after mating such that corresponding first and second openings 110, 112 in said first and second terminal end surfaces 104, 108 are mated aseptically. The films 114 can e.g. be folded over and be connected to, or form, tabs protruding outside the connection units, which makes the tabs suitable for pulling.

In the first embodiment disclosed in FIG. 1, two first ports 116 are arranged on the first connection unit 102, which first ports 116 have fluid connection with respective first opening 110 in the first terminal end surface 104. The fluid connection between the first ports 116 and the first openings 110 forms a respective first passage 117 for fluids. On the second connection unit 106 two second ports 118 are arranged, which second ports 118 have a fluid connection with respective second opening 112 in the second terminal end surface 108. The fluid connection between the second ports 118 and the second openings 112 forms a respective second passage 119 for fluids. Therefore, according to the first embodiment the number of openings 110, 112 in the respective terminal end surface 104, 108 corresponds to the number of ports 118, 116 arranged on the connection unit 102, 106.

Pipes or tubes 120, such as flexible thermoplastic tubes are intended to be connected to the ports 116, 118 by pushing them over the projecting ports 116, 118, so that a mechanical retention of the pipes or tubes 120 is achieved in order to form a leak-tight seal. The pipes or tubes 120 may also be connected to process containers and equipment, such as plastic bags and pumps (not disclosed). The ports 116, 118 may have equal or different diameters, so that the aseptic connector 100 is applicable to a wide array of pipe and tube 120 sizes. In the embodiment disclosed the ports 116, 118 projects out of the connection units 102, 106. However, it is also possible to arrange the ports 116, 118 as apertures (not disclosed) in the connection unit 102, 106, so that the pipes or tubes 120 are pushed into and installed in the aperture.

A gasket 122 is arranged around each opening 110, 112. Said gasket 122 being adapted to mate with a corresponding gasket 122 or terminal end surface 104, 108 on the other connection unit 102, 106 which the connection unit 102, 106 possibly should be connected with when the films 114 have been released from the connection units 102, 106. The gasket 122 can possibly also be arranged around a suitable number of openings 110, 112. Also, a foam layer 124, such as a compressible foam layer, is arranged around each gasket 122, which foam layer 124 is adapted to be compressed around each gasket 122 when two connection units 102, 106 are mated. The foam layer 124 provided around the gaskets 122 leads to that the units can be pressed together to a first aseptic connection position where the protective films 114 can be removed without exposing the aseptic process side to the environment, which may be non-sterile. The purpose of the compressible foam layers 124 is to provide the required degree of volumetric variability to allow for an expansion of the two opposite foam layers 124 against each other to remain asepsis when removing the adjacent folded films 114 by pulling.

In FIG. 1 the films 114 are double folded over said openings 110, 112 and a single sheet of the uppermost layer of the film 114 is reaching outside the terminal end surfaces 104, 108 and adapted to be pulled together with another single sheet of another film 114 when the films 114 are released from the connection units 102, 106. The film 114 is suitably provided to the units 102, 106 before the units are subjected to sterilisation. This means that the connection unit 102, 106 with the attached film 114 can be treated in a non sterile environment while the contents of the connection unit 102, 106 confined by its openings and ports including the openings and ports still are kept sterile or aseptic. In FIG. 1 only one film 114 is arranged in each terminal end surface 104, 108. It is however possible to arrange films 114 for each opening in the terminal end surface 104, 108. The connection units 102, 106 are provided with orientation specific locking means 126 arranged to mechanically lock the connection units 102, 106 to each other.

Figure 2:
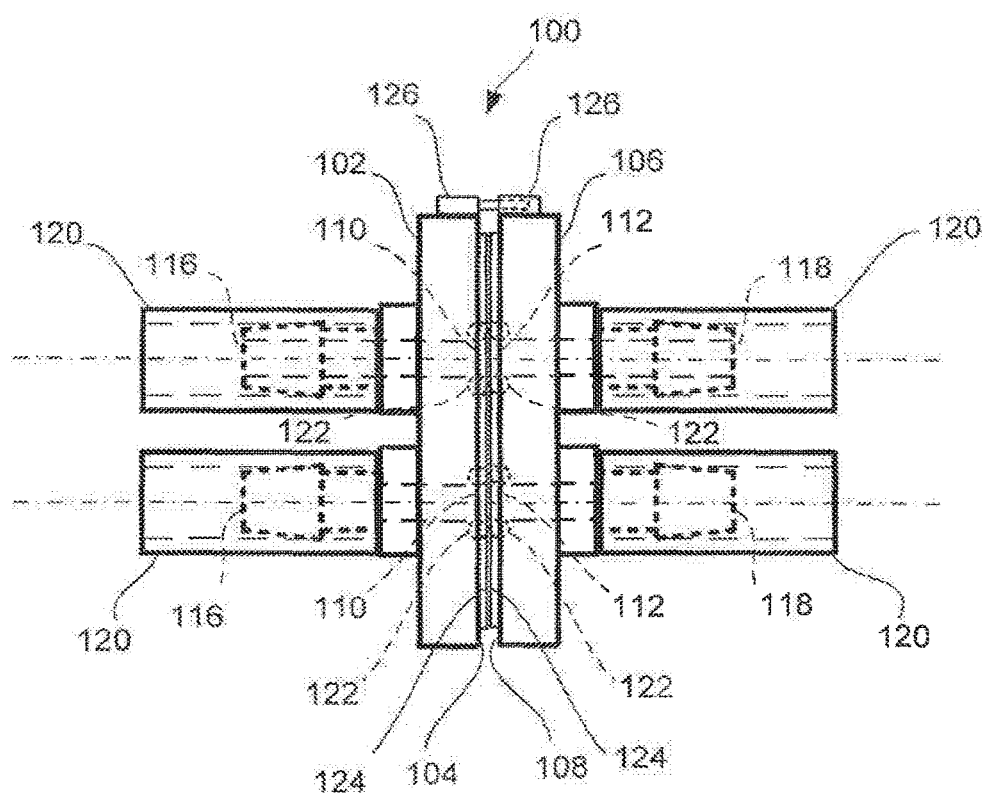
FIG. 2 shows a side view of the first embodiment of the aseptic connector in FIG. 1.

FIG. 2 shows the first embodiment of the aseptic connector 100 when the first and 25 second connection units 102, 106 are connected. In this position the locking means 126 mechanically locks the connection units 102, 106 to each other. The openings are orientated to substantially coincide when said first and second connection units 102, 106 are connected to each other, which is disclosed in FIG. 2.

Figure 3:
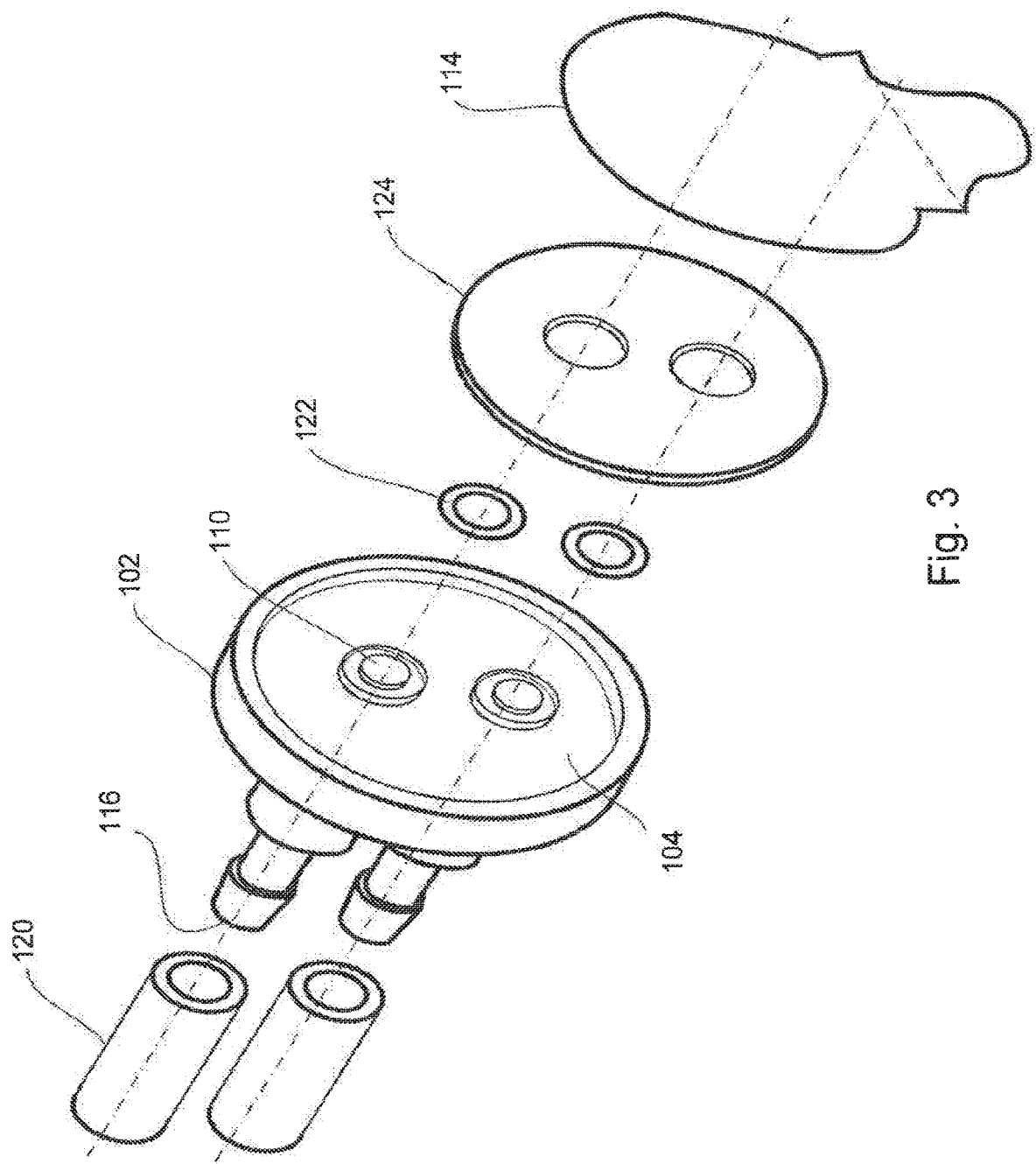
FIG. 3 shows a first connection unit according to the first embodiment in perspective.

FIG. 3 shows a first connection unit 102 according to the first embodiment in perspective. In the first terminal end surface 104, two first openings 110 are provided. The first openings 110 are arranged to be sealed by the film 114 arranged on the first connection unit 102, so that the contact between the film 114 and the first connection unit 102 is aseptic. Two first ports 116 are arranged on the first connection unit 102, which first ports 116 have fluid connection with the respective first opening 110 in the first terminal end surface 104. A gasket 122 is arranged around each first opening 110 and a foam layer 124 is arranged around each gasket 122, which foam layer 124 is adapted to be compressed around each gasket 122 when two connection units are mated.

Figure 4:
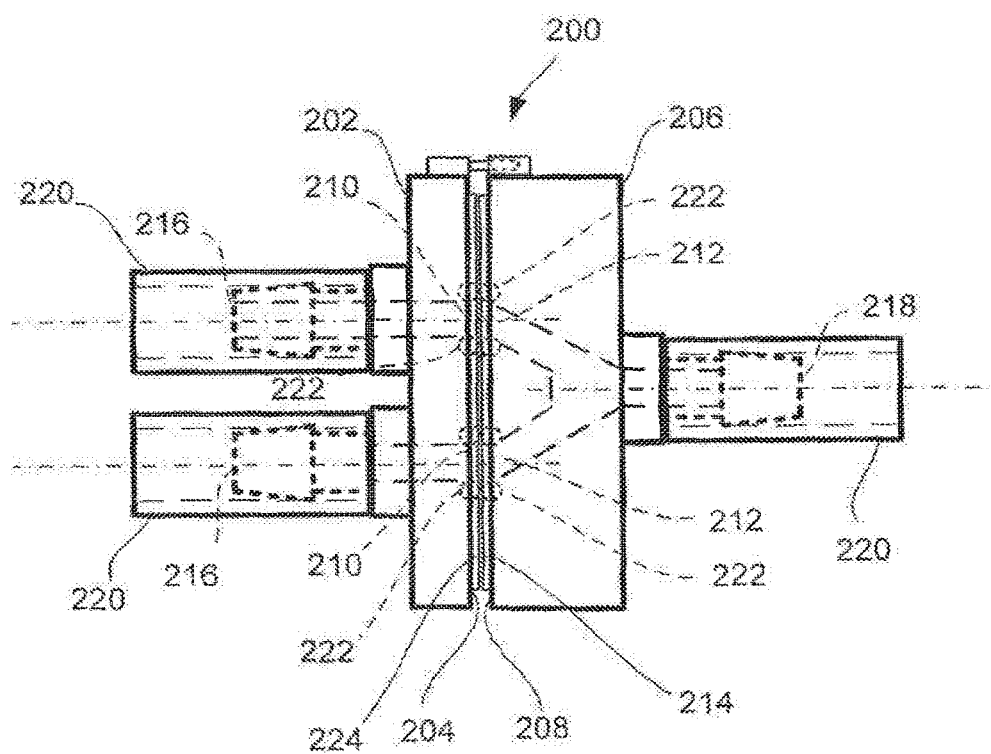
FIG. 4 shows a side view of a second embodiment of an aseptic connector according to the invention.

FIG. 4 shows an aseptic connector 200 according to a second embodiment of the present invention. In this second embodiment two first ports 216 are arranged on the first connection unit 202, which first ports 216 have fluid connection with two first openings 210 in the first terminal end surface 204. On the second connection unit 206 only one second port 218 is arranged, which has a fluid connection with two second openings 212 in the second terminal end surface 208. The first and second openings 210, 212 are orientated to substantially coincide when said first and second connection units 202, 206 are connected to each other. In FIG. 4 the films 214 are removed, so that the gaskets 222 arranged around each opening 210, 212 mates with a corresponding gasket 222 on the other connection unit which the connection unit possibly should be connected with when the films 214 have been released from the connection units 202, 206. Also, the foam layers 224 arranged around each gasket 222 are compressed when the two connection units 202, 206 are mated. The aseptic connector 200 according to this second embodiment is arranged as a manifold.

Figure 5:
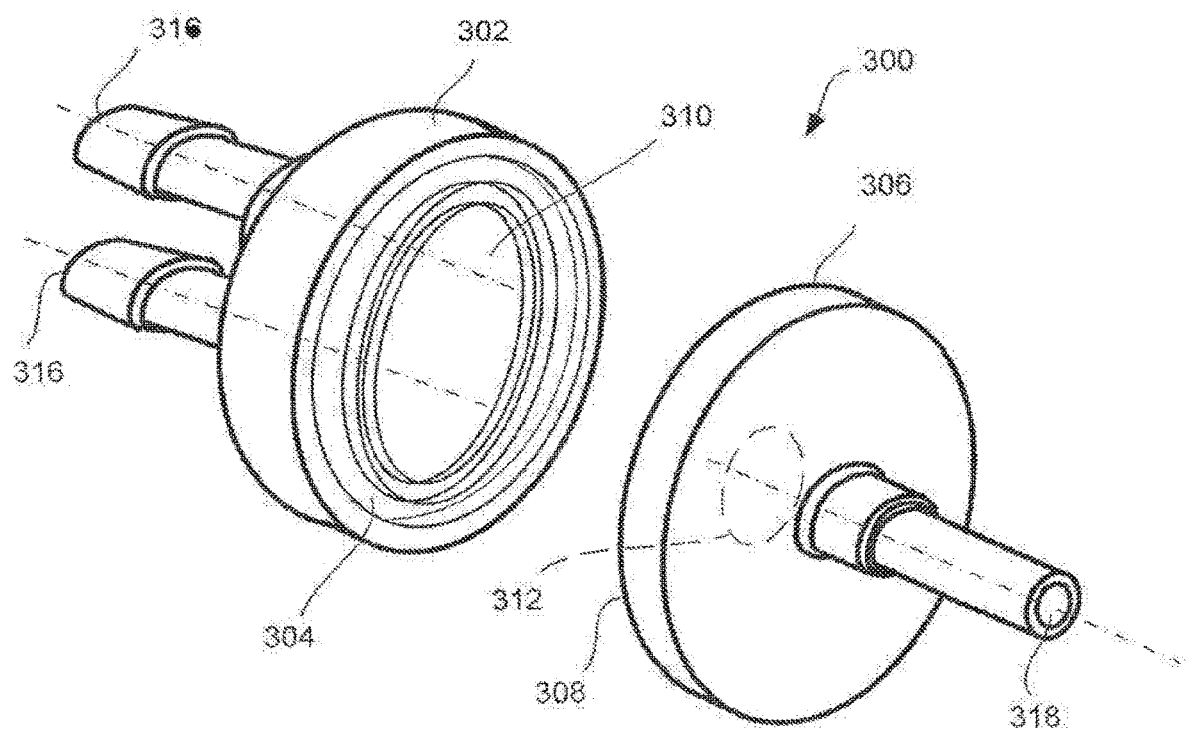
FIG. 5 shows a view in perspective of a third embodiment of an aseptic connector according to the invention.

FIG. 5 shows an aseptic connector 300 according to a third embodiment of the present invention in perspective. In this third embodiment two first ports 316 are arranged on the first connection unit 302, which first ports 316 have fluid connection with only one first opening 310 in the first terminal end surface 304. On the second connection unit 306 only one second port 318 is arranged, which has a fluid connection with only one second opening 312 in the second terminal end surface 308. The first and second openings 310, 312 are orientated to substantially coincide when said first and second connection units 302, 306 are connected to each other.

Figure 6:
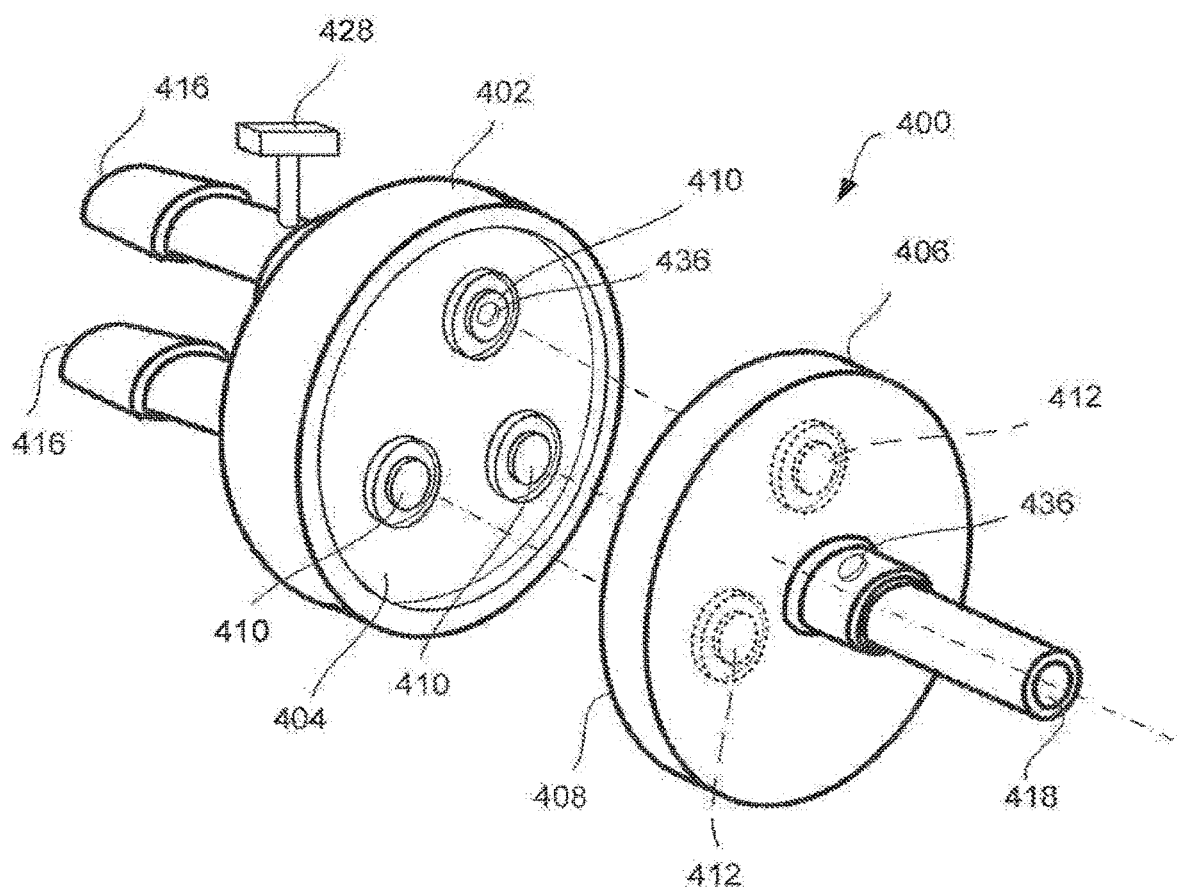
FIG. 6 shows a view in perspective of a fourth embodiment of an aseptic connector according to the invention.

FIG. 6 shows an aseptic connector 400 according to a fourth embodiment of the present invention in perspective. In this fourth embodiment three first ports 416 are arranged on the first connection unit 402, which first ports 416 have fluid connection with three first openings 410 in the first terminal end surface 404. On the second connection unit 406 only one second port 418 is arranged, which has a fluid connection with three second openings 412 in the second terminal end surface 408. The first and second openings 410, 412 are orientated to substantially coincide when said first and second connection units 402, 406 are connected to each other. In this embodiment also at least one of the first ports 416 is provided with a valve 428, which is arranged to control fluid flow through the first connection unit 402 and the aseptic connector 400. The valve 428 can be of the type which opens and closes the port 416. However, it is also possible to arrange the valve as a three-way valve (not disclosed).

In FIG. 6 the aseptic connector 400 may be provided with measuring means 436 comprising sensors for measuring and monitoring for example pressure, velocity in flow, temperature and conductivity. Also, radio frequency identification (RFID) tags may be used in combination with the sensors in the measuring means 436. The measuring means 436 may be located within the connector 400 and in contact with the fluid in the connector 400, or located on a location outside the connector 400. The RFID tags may communicate with a computer (not disclosed) for collecting information about the measured values. Preferred geometries of the measurement means 436 are round or circular, but other geometries can be used for similar purposes.

Figure 7:
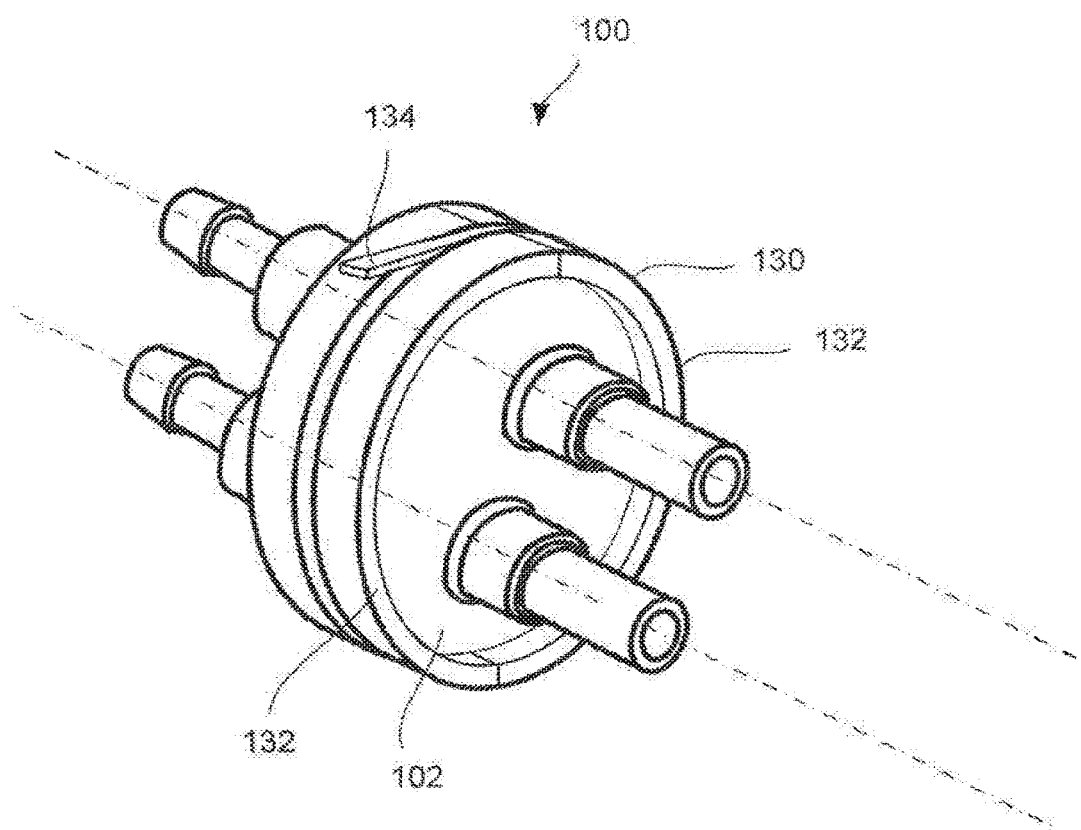
FIG. 7 shows a view in perspective of the first embodiment of the aseptic connector according to the invention provided with a clamp means.

In FIG. 7 the aseptic connector 100 according to the first embodiment is provided with a clamp 130, which at least partially encloses the connector 100. The clamp 130 comprises two shells 132 which are arranged at the periphery of first and second connection units 102, 106 and locked with a strap 134. The clamp 130 urges the first and second connection units 102, 106 in a direction to each other and prevents any leakage of fluid from the aseptic connector 100. The clamp 130 also prevents the first and second connection units 102, 106 to be unintentional disconnected.

Figure 8:
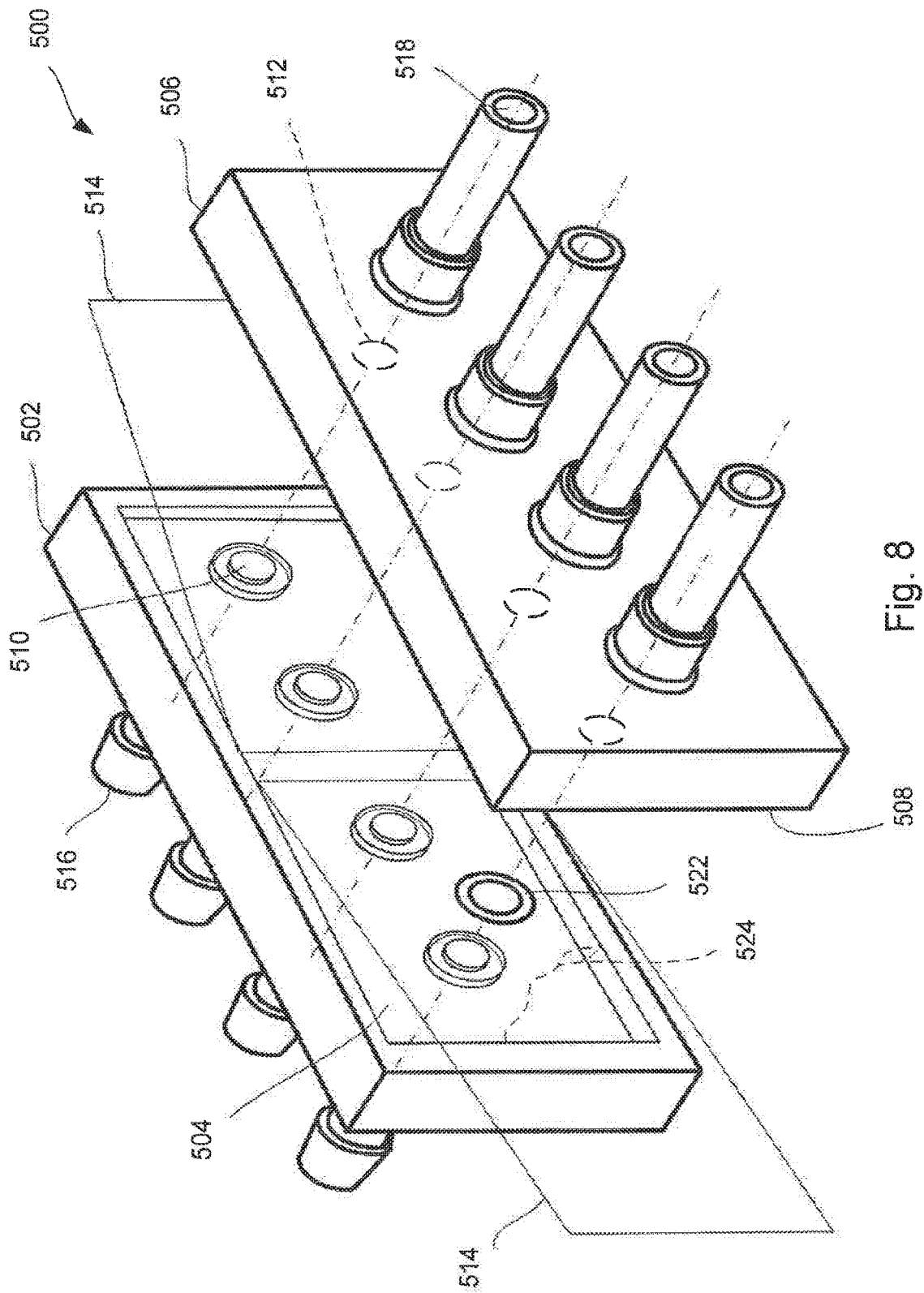
FIG. 8 shows a view in perspective of a fifth embodiment of an aseptic connector according to the invention.

FIG. 8 shows an aseptic connector 500 according a fifth embodiment. In addition to the first embodiment above the aseptic connector 500 according the fifth embodiment has four first ports 516 arranged on the first connection unit 502, which first ports 516 have fluid connection with four first openings 510 in the first terminal end surface 504. On the second connection unit 506 also four second ports 518 are arranged, which have a fluid connection with four second openings 512 in the second terminal end surface 508. The first and second openings 510, 512 are orientated to substantially coincide when said first and second connection units 502, 506 are connected to each other. The first and second openings 510, 512 are sealed by films 514 arranged on said first and second connection units 502, 506. A gasket 522 is arranged around each first opening and a foam layer 524 is arranged around each gasket 522. In the fifth embodiment the films 514, gaskets 522 and foam layer 524 are disclosed when arranged at the second connection unit 506. However, films 514, gaskets 522 and foam layer 524 are also arranged at the first connection unit 502, but not disclosed in FIG. 8. The first and second connection units 502, 506 according to the fifth embodiment have a substantial rectangular configuration in comparison to the substantial circular configuration of the connection units in the embodiments above.

Preferably, the aseptic connector 100; 200; 300; 400; 500 according to the invention is a disposable unit, i.e. adapted to be used only once. One advantage with disposable systems is that there is no need for cleaning and bioburden control before using the systems because disposable systems are already aseptic in some degree and they should not be used again and need therefore not be cleaned between uses. Therefore the aseptic connector 100; 200; 300; 400; 500 according to this invention is particularly interesting in disposable systems.

In a further aspect of the invention, a sterile circuit is disclosed, which comprises at least one first connector unit 102; 202; 302; 402; 502 as discussed above and at least two lengths of tubing 120; 220 fluidically connected to the unit, preferably to the ports 116; 118; 216; 316; 416; 516; 518. The sterile circuit may be presterilized, e.g. by irradiation or autoclaving and it may be packaged in a sterile container, such as e.g. a sterile pouch or bag. The sterile circuit may further comprise at least one container, such as a storage bag or a bioreactor bag, which is fluidically connected to at least one of the tubing lengths 120; 220. The first connector unit of the sterile circuit may be aseptically connected to a second connector unit, which may, or may not, form a part of a second sterile circuit with at least one length of tubing fluidically connected to the second connector unit.

The provision of sterile circuits greatly facilitates the setup of complex sterile systems, such as bioreactors with multiple lines for feeding nutrients, gases etc and for removal of culture fluid and/or metabolites etc. One sterile circuit may be attached to one bioreactor via one or more lengths of tubing or it may be attached to a plurality of bioreactors. The latter is particularly suitable for screening experiments such as high throughput screening experiments where a large number of small bioreactors are used and it is of imperative need to have a compact system for supply and removal of fluids.

The word aseptic used in this description and in the claims shall have a broad definition, i.e. include any level of bioburden control. The bioburden control or asepsis can be measured as organisms/ml or CFU (colony forming units). In one embodiment of the invention the level of asepsis should be below 100 CFU/ml. The latter corresponds to bioburden control levels required for food grade products. Low levels of bioburden can be achieved by sterilisation processes. For example the aseptic connector 100; 200; 300; 400; 500 of the invention can be subjected to gamma sterilization. Other possible methods are autoclaving or bioburden control by ethylene dioxide.

In all embodiments described above parts and surfaces being in contact with a process fluid are suitably selected from materials that are in accordance with typical material requirements in (bio-)pharmaceutical manufacturing or food grade quality. For example, materials are suitably in compliance with USP Class VI and 21 CFR 177. Furthermore they are suitably of animal-free origin and compliance to EMEA/41O/01.

Features and components of the different embodiments above may be combined within the scope of the invention.

What is claimed is:

1. An aseptic manifold comprising,
   a first connection unit having a first side and a second side that is opposite to the first side, wherein the first side of the first connection unit comprises at least two first ports and the second side of the first connection unit comprises a first terminal end surface, wherein the first terminal end surface is provided with at least two first openings sealed by a first film and each first opening is in fluid communication with a corresponding first port, and
   a single piece second connection unit having a first side and a second side that is opposite to the first side, wherein the first side of the second connection unit comprises one second port and the second side of the second connection unit comprises a second terminal end surface, wherein the second terminal end surface is provided with at least two second openings sealed by a second film and the second openings each extend inside the second connection unit forming two conduits that merge into a single conduit inside the second connection unit to be in fluid communication with the one second port,
   wherein each of the first two openings is positioned to coincide respectively with the two second openings when the units are connected, and
   wherein the first film of the first connection unit is adapted to be mated with the second film of the second connection unit such that when the first and the second connection units are connected to each other the mated films are adapted to be pulled out together to allow the first and second terminal end surfaces to mate aseptically.

2. The aseptic manifold of claim 1, wherein the aseptic manifold is a disposable unit.

3. The aseptic manifold of claim 1, wherein a gasket is arranged around each opening and a gasket around a first opening of the at least two first openings is adapted to mate with a corresponding gasket around a second opening of the at least two first openings when the first and the second connection units mate with each other such that each first opening is sealingly connected with its corresponding second opening.

4. The aseptic manifold of claim 3, wherein a first foam layer is arranged around each gasket of the first terminal surface and a second foam layer is arranged around each gasket of the second terminal surface such that the first foam layer is adapted to be compressed with the second foam layer when two connection units are mated.

5. The aseptic manifold of claim 1, wherein the first film has a first portion covering the first openings and another portion folded over the first portion forming a single sheet reaching outside the first terminal end surface as a first tab and the second film has a first portion covering the second openings and another portion folded over the first portion forming a single sheet reaching outside the second terminal end surface as a second tab and the first tab and the second tab are adapted to be pulled together to release the films from the connection units.

6. The aseptic manifold of claim 1, wherein at least one of the first and second ports is provided with a valve, which is arranged to control fluid flow through the aseptic manifold.

7. The aseptic manifold of claim 1, further comprising measuring means that comprises a sensor with RFID tag arranged at the aseptic manifold.

8. The aseptic manifold of claim 1, wherein the connection units are provided with orientation specific locking means arranged to mechanically lock the connection units to each other.

9. The aseptic manifold of claim 1, wherein the at least two first openings of the first terminal surface comprise two first openings, and the at least two first openings of the second terminal surface comprise two second openings that coincide with the two first openings when the units are connected.

10. The aseptic manifold of claim 1, wherein the two conduit of the two second openings merge into the single conduit, forming a "Y" branching inside the single piece second connection unit.

11. A sterile circuit comprising at least two lengths of tubing each fluidically connected to one of the at least two ports of the first connection unit of claim 1.

12. The sterile circuit of claim 11, further comprising a container fluidically connected to the at least two lengths of tubing.

13. An aseptic manifold comprising,
a first connection unit having a first side and a second side that is opposite to the first side, wherein the first side of the first connection unit comprises two first ports and the second side of the first connection unit comprises a first terminal end surface, wherein the first terminal end surface is provided with two first openings sealed by a first film and each first opening is in fluid communication with a corresponding first port, and
a single piece second connection unit having a first side and a second side that is opposite to the first side, wherein the first side of the second connection unit comprises one second port and the second side of the second connection unit comprises a second terminal end surface, wherein the second terminal end surface is provided with two second openings sealed by a second film and the second openings are in fluid communication with the one second port, wherein the two second openings each extend inside the second connection unit, forming two conduits that merge into a single conduit, forming a "Y" inside the second connection unit to be in fluid communication with the one second port,
wherein each of the first two openings is positioned to coincide respectively with the two second openings when the units are connected,
wherein the first film of the first connection unit is adapted to be mated with the second film of the second connection unit such that when the first and the second connection units are connected to each other the mated films are adapted to be pulled out together to allow the first and second terminal end surfaces to mate aseptically,
wherein a gasket is arranged around each opening and a gasket around a first opening of the two first openings is adapted to mate with a corresponding gasket around a second opening or the two first openings when the first and the second connection units mate with each other such that each first opening is sealingly connected with its corresponding second opening,
wherein a first foam layer is arranged around each gasket of the first terminal surface and a second foam layer is arranged around each gasket of the second terminal surface such that the first foam layer is adapted to be compressed with the second foam layer when two connection units are mated,
wherein the first film has a first portion covering the first openings and another portion folded over the first portion forming a single sheet reaching outside the first terminal end surface as a first tab and the second film has a first portion covering the second openings and another portion folded over the first portion forming a single sheet reaching outside the second terminal end surface as a second tab and the first tab and the second tab are adapted to be pulled together to release the films from the connection units.

14. The aseptic manifold of claim 13, wherein at least one of the first and second ports is provided with a valve, which is arranged to control fluid flow through the aseptic manifold.

15. The aseptic manifold of claim 13, further comprising measuring means that comprises a sensor with an RFID tag arranged at the aseptic manifold.

16. The aseptic manifold of claim 13, wherein the connection units are provided with orientation specific locking means arranged to mechanically lock the connection units to each other.

17. A sterile circuit comprising two lengths of tubing each connected to one of the two ports of the first connection unit of claim 13.

18. The sterile circuit of claim 17, further comprising a container fluidically connected to the at least two lengths of tubing.

* * * * *

UNITED STATES PATENT AND TRADEMARK OFFICE
CERTIFICATE OF CORRECTION

PATENT NO. : 10,946,183 B2
APPLICATION NO. : 15/625401
DATED : March 16, 2021
INVENTOR(S) : Eric Faldt and Klaus Gebauer Page 1 of 1

It is certified that error appears in the above-identified patent and that said Letters Patent is hereby corrected as shown below:

In the Claims

At Column 10, Line 15, delete "or" and insert --of--.

Signed and Sealed this
First Day of June, 2021

Drew Hirshfeld
*Performing the Functions and Duties of the
Under Secretary of Commerce for Intellectual Property and
Director of the United States Patent and Trademark Office*